United States Patent [19]

Brent

[11] Patent Number: 5,124,125
[45] Date of Patent: Jun. 23, 1992

[54] METHOD FOR PROCESSING INFECTIOUS WASTE USING MICROWAVES

[76] Inventor: David A. Brent, L-163 Groffs Mill Rd., Harleysville, Pa. 19438

[21] Appl. No.: 550,469

[22] Filed: Jul. 10, 1990

[51] Int. Cl.$^5$ .............................................. A61L 2/12
[52] U.S. Cl. ...................................... 422/21; 422/26; 422/32; 422/33; 422/39
[58] Field of Search ...................... 422/21, 26, 32, 33, 422/39, 295, 297; 423/DIG. 18, DIG. 20

[56] References Cited

U.S. PATENT DOCUMENTS

| | | | |
|---|---|---|---|
| 4,374,491 | 2/1983 | Stortroen et al. | 100/73 |
| 4,623,515 | 11/1986 | Frei et al. | 422/32 |
| 4,644,586 | 2/1987 | Padgett | 383/102 |
| 4,670,227 | 6/1987 | Smith | 422/297 |
| 4,896,010 | 1/1990 | O'Connor et al. | 422/21 |

FOREIGN PATENT DOCUMENTS 0031790 7/1981 European Pat. Off. ............. 422/26

OTHER PUBLICATIONS

Ready, Tinker; "Hospital Waste Meets Match as Microwave Zaps Infection"; pub. in *Raleigh News and Observer*, Dec. 30, 1990, p. C1.
Marbach, William D., ed.; "Nuking Nasty Medical Waste—in a Microwave"; pub. in *Business Week*, Jul. 23, 1990, Science & Technology Section.

*Primary Examiner*—Robert J. Warden
*Assistant Examiner*—Laura E. Collins
*Attorney, Agent, or Firm*—Richard E. Jenkins

[57] ABSTRACT

A method for microwave sterilization and densification of infectious waste wherein a supply of infectious waste to be sterilized and disposed of is provided which includes at least 20% by weight of plastic materials. A selected portion of the infectious waste is placed into a pressure vessel of a microwave sterilizer and then the sterilizer is sealed. A selected amount of water is then introduced into the sealed pressure vessel to facilitate treatment of the infectious waste contained therein, and the microwave sterilizer is actuated in order to transform the water in the pressure vessel into steam to elevate the temperature within the pressure vessel to at least 150° C. and the pressure to at least 54 p.s.i.g. The infectious waste within the pressure vessel is sterilized and then densified by melting the plastic materials contained therein to form a unitary mass of reduced volume wherein the melted plastic substantially encases the residual sterilized infectious waste components.

26 Claims, 4 Drawing Sheets

METHOD FOR PROCESSING INFECTIOUS WASTE USING MICROWAVES

DESCRIPTION

1. Technical Field

The present invention relates to waste disposal systems, and more particularly to a method and apparatus for processing infectious waste such as biohazardous materials contaminated with bacteria, fungi, and viruses such as AIDS and Hepatitis B.

2. Related Art

Infectious waste materials from sources such as hospitals and research laboratories present a particularly grave danger to those involved in disposing of the materials and, if the disposal is not handled properly, to those who may be subsequently exposed to the discarded infectious waste. This is particularly true today in view of the greater likelihood of contamination of the infectious waste or biohazardous materials with the AIDS and Hepatitis B viruses.

Up to this time, infectious waste has been processed by storing containers of the infectious waste in a suitable storage facility and then from time to time either transporting the containers to an incinerator or to an autoclave for sterilization. Normally, the waste product from the incinerator or steam autoclave must then be collected and taken to a landfill for final disposal. Unfortunately, as is well known to those familiar with infectious waste disposal, the collected infectious waste materials may sometimes be taken directly to a landfill for disposal prior to sterilization or decontamination thereof and present a potentially grave health risk to those in the immediate environment of the disposal site.

In view of the limitations of processing infectious waste materials in either conventional incinerators or steam autoclaves, there is clearly a great need for an improved manner to deal with the ever increasing volume and attendant danger of infectious waste materials.

SUMMARY OF THE INVENTION

The present invention generally comprises a system for processing infectious waste materials (including those contaminated with bacteria, fungi, and AIDS and Hepatitis B viruses) which is particularly designed to efficiently decontaminate infectious waste and render it suitable for subsequent disposal in a landfill site or the like. The apparatus and method of the invention are safe and effective when compared to conventional techniques, and the resulting sterilized infectious waste is a unitary product of significantly reduced volume which is particularly well adapted for disposal in a landfill site.

The apparatus comprises a pressure vessel which is adapted to be opened to receive the infectious waste to be treated and to then be sealingly closed during the treatment process. Microwave energy producing means is provided adjacent the pressure vessel and positioned so as to focus the microwave energy produced thereby on a predetermined location within the pressure vessel where the infectious waste will be received for treatment. Means for introducing water into the sealed pressure vessel is provided to facilitate treatment of the infectious waste therein, and monitoring means is provided to determine the temperature and pressure within the pressure vessel during operation of the microwave autoclave apparatus of the invention.

The method of the invention contemplates providing a supply of infectious waste to be sterilized and disposed of which includes at least 20% by weight of plastic materials therein. A selected portion of the infectious waste is placed into the pressure vessel of a microwave sterilizer, and the microwave sterilizer is then sealed shut. Next, a selected amount of water is introduced into the sealed pressure vessel, and the microwave sterilizer is actuated so as to transform the water in the pressure vessel into steam and to thereby elevate the temperature to at least 150° C. and the pressure to at least 54 psig. The infectious waste is sterilized and then densified within the pressure vessel due to the melting of the plastic materials contained therein to form a unitary mass of reduced volume wherein the melted plastic substantially encases the residual sterilized infectious waste components. Finally, the unitary mass of hazardous waste is removed from the microwave sterilizer and disposed of.

It is therefore the object of this invention to provide a method and apparatus for handling biologically infectious waste materials which prevents contamination from the waste materials during treatment and disposal thereof.

Another object of the present invention is to provide a method and apparatus to aid in disinfecting and disposing of biologically infectious waste materials which more effectively sterilizes the infectious waste materials.

It is another object of the present invention to provide a method and apparatus for treatment and disposal of infectious waste materials which produces a densified end product of significantly reduced volume which is particularly adapted for ease of handling during disposal thereof.

Some of the objects of the invention having been stated, other objects will become evident as the description proceeds, when taken in connection with the accompanying drawings described below.

BEST MODE FOR CARRYING OUT THE INVENTION

The present invention generally comprises an apparatus and method for processing biologically infectious waste material including (but not limited to) infectious waste materials contaminated with bacteria, fungi and virus, particularly AIDS and Hepatitis B virus. The invention provides for more effective sterilization of the infectious waste materials as well as the alteration of the form of the processed materials to a significantly volume-reduced form for ease of final disposal.

Of interest, a listing of EPA recommended categories of infectious waste is set forth below for a more complete understanding of the invention. The categories include the following:

| Waste Category | Examples |
| --- | --- |
| 1. Isolation wastes | Refer to Centers for Disease Control (CDC), Guidelines for Isolation Precautions in Hospitals, July 1983 |
| 2. Cultures and stocks of infectious agents and associated biologicals | Specimens from medical and pathology laboratories Cultures and stocks of infectious agents from clinical, research, and industrial laboratories; disposable culture dishes; and devices used to transfer, inoculate and mix cultures Wastes from production of biologicals Discarded live and attenuated vaccines |
| 3. Human blood and blood products | Waste blood, serum, plasma, blood products |
| 4. Pathological waste | Tissues, organs, body parts, blood, and body fluids removed during surgery, autopsy, and biopsy |
| 5. Contaminated sharps | Contaminated hypodermic needles, syringes, scalpel blades, pasteur pipettes, and broken glass |
| 6. Contaminated animal body parts and bedding | Contaminated animal carcasses, body parts, and bedding of animals that were intentionally exposd to pathogens |
| 7. Miscellaneous Contaminated Wastes | |
| a. Wastes from surgery and autopsy | Soiled dressings, sponges, drapes, lavage tubes, drainage sets, underpads, and surgical gloves |
| b. Miscellaneous laboratory wastes | Specimen containers, slides, and cover slips; disposable gloves, lab coats |
| c. Dialysis unit wastes | Tubing, filters, disposable sheets, towels, gloves, aprons, and lab coats |
| d. Contaminated equipment | Equipment used in patient care, medical laboratories, research, and in the production and testing of certain pharmaceuticals |

It is also contemplated that the apparatus and method of the invention can be used to destroy organisms which have been genetically engineered.

Figure 1:
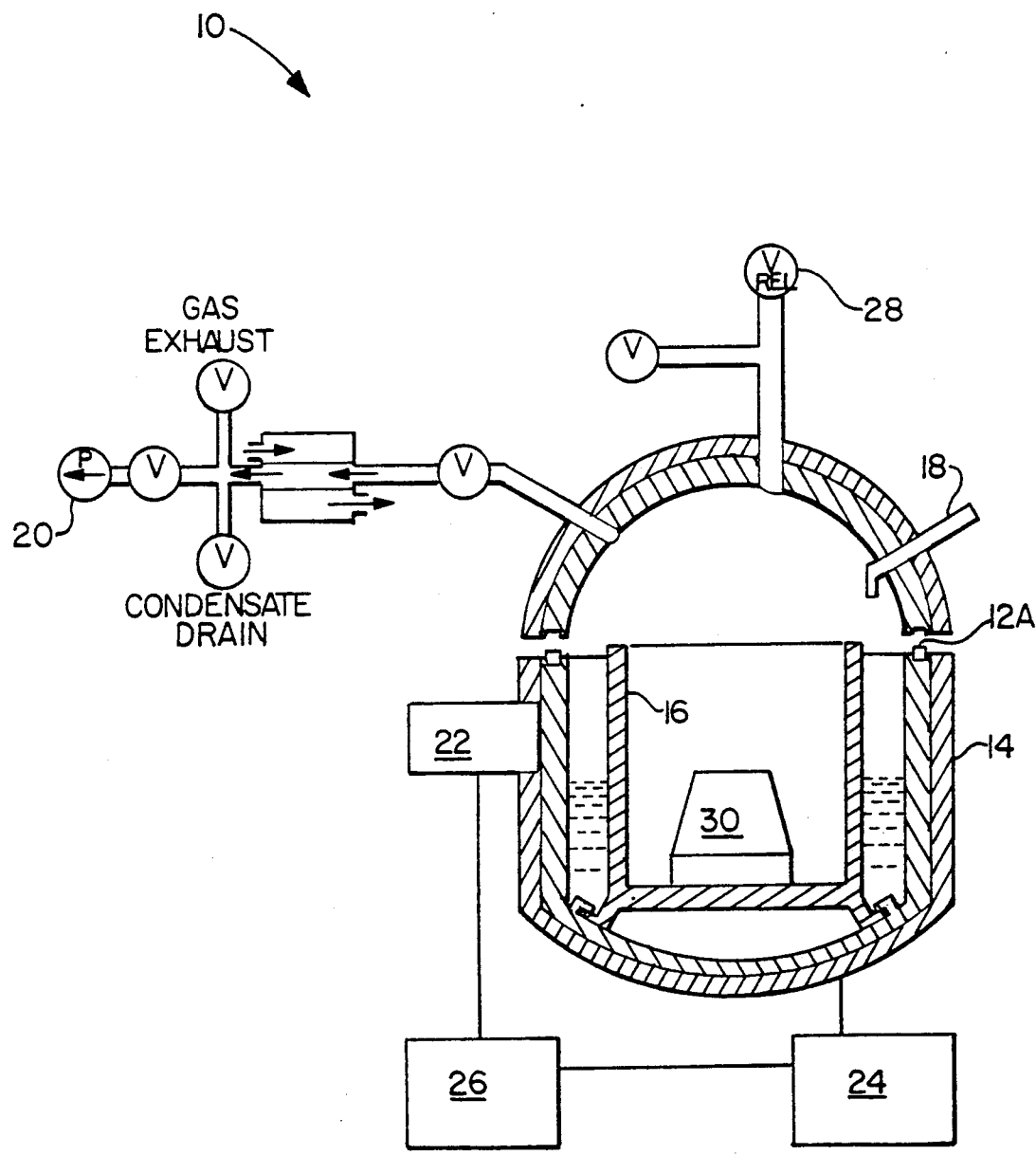
FIG. 1 is a schematic view of an apparatus for handling of infectious waste in accordance with the present invention.

As best seen in FIG. 1, microwave autoclave apparatus 10 comprises a pressure vessel 12 which is preferably constructed of a high strength plastic such as liquid crystal polymers (LCP) or thermoplastic composite materials utilizing carbon or glass to provide high impact strength. LCP's which could suitably be used to manufacture pressure vessel 12 are available from such companies as Amoco, BASF, DuPont, Hoechst, Celanese, and ICI under various tradenames. The plastic would either have to be reflective to microwave energy or, if transparent thereto, would require a microwave reflective metal outside shell 14. The use of high strength plastic for pressure vessel 12 offers low cost and high thermal and pressure stability. In the alternative, however, pressure vessel 12 could also be constructed of a metal such as stainless steel which would reflect microwave energy.

Microwave autoclave apparatus 10 includes a removable pressure vessel insert 16 for containment of infectious waste material therein. Pressure vessel insert 16 is most suitably formed from a microwave transparent material (such as high strength plastic) and is intended to be disposable in view of likely periodic damage from the processing treatment of infectious waste therein. Water inlet 18 is provided through metal shell 14 and pressure vessel 12 to allow for the introduction of water into pressure vessel 12 after infectious waste has been placed therein and pressure vessel 12 sealed by means of compression seal 12A. Optionally, water inlet 18 can also be used to introduce water into pressure vessel 12 after treatment of the infectious waste so as to create steam which is allowed to escape the pressure vessel through suitable means such as petcocks (not shown).

Although microwave autoclave apparatus 10 may be operated with the air therein, most suitably the air is withdrawn by vacuum pump 20 which fluidly communicates with the interior of pressure vessel 12. Removal of the air allows for a lower psig pressure to achieve a specific temperature and obviates air pockets in the infectious waste which can be a cause of ineffective waste sterilization.

In order to heat the water introduced into pressure vessel 12 to form the steam necessary for waste sterilization, a suitable microwave energy source 22 is positioned adjacent pressure vessel 12 and focused on the location therein where the infectious waste will be placed. Although any suitable microwave power source may be utilized as a matter of choice, applicant prefers that a 915 MHz or 2.4 GHz magnetron be used. Monitor 24 is provided to monitor processing parameters such as time, temperature, pressure, humidity, and reflected microwave energy. Although the means to do so are a matter of design choice, the temperature may be monitored by, for example, thermistors or fiber optic thermometers placed in or adjacent to the infectious waste being treated. The pressure, humidity, time, and reflected microwave energy can be monitored external to the microwave field created by microwave energy source 22 using conventional measurement devices. Also, the pressure can be measured directly on the vessel by using an oil-filled tube and diaphragm apparatus with a remote transducer outside of the microwave field.

Figure 3:
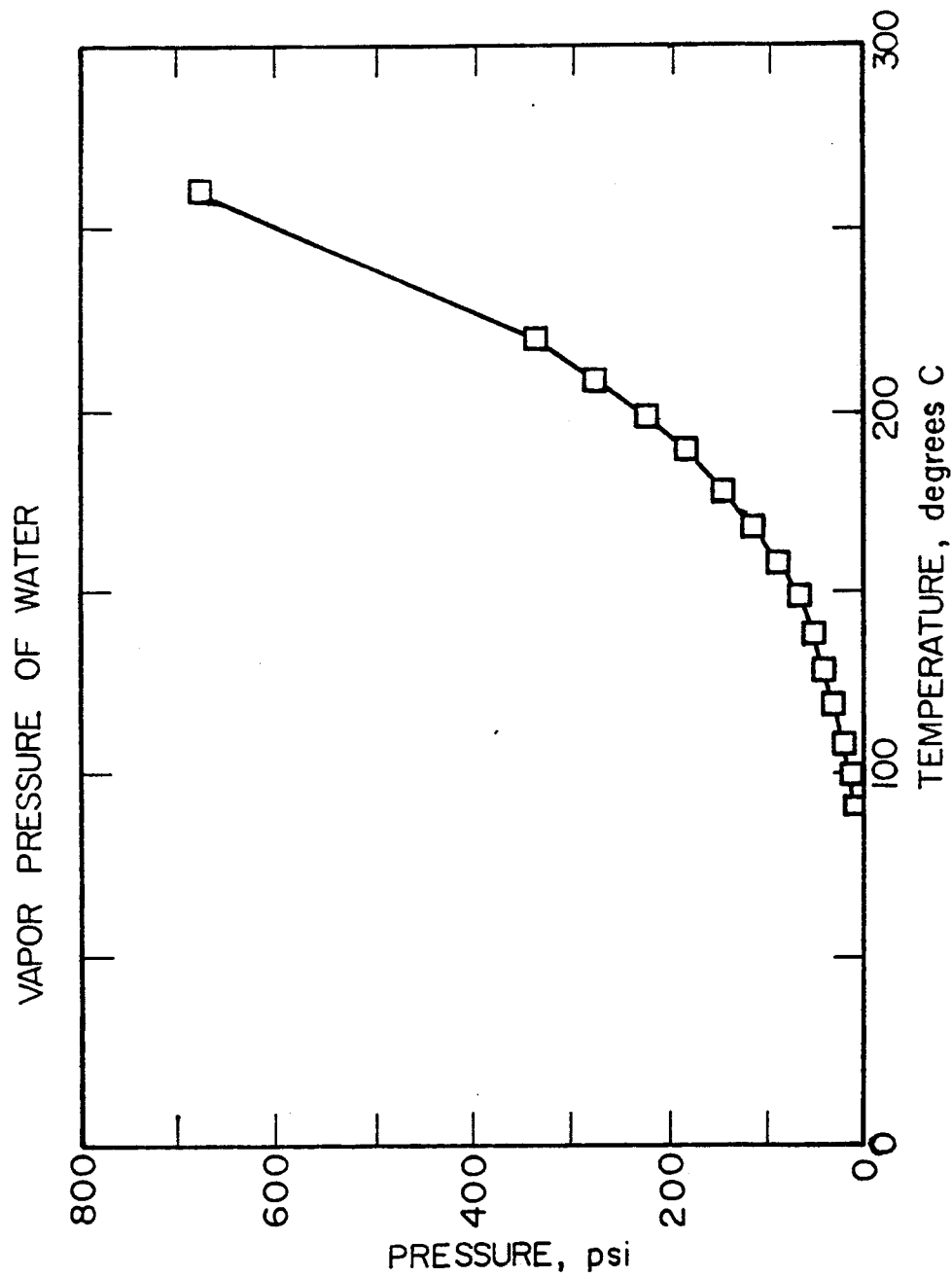
FIG. 3 is a chart illustrating the effect of temperature on vapor pressure.

Since pressure rises exponentially with temperature (see FIG. 3), a suitable microprocessor 26 is electrically connected to microwave energy source 22 and monitor 24 so that when a predetermined temperature is reached (for example 200° C.), microprocessor 26 will deactuate microwave energy source 22. As an additional safety mechanism, a pressure relief valve and system vent 28 are provided.

If desired, applicant further contemplates that a steam generator (not shown) could be used in conjunction with microwave energy source 22 to treat infectious waste in apparatus 10.

Most suitably, infectious waste is placed into a waste container 30 prior to placement into pressure vessel insert 16 of pressure vessel 12, although infectious waste may be placed directly in loose form into pressure vessel insert 16 for treatment. Waste container 30 may be any suitable container such as a plastic bag that will melt during the autoclave process (for example, a 3 mil thick polyethylene or polystyrene plastic bag). Also, waste container 30 may suitably comprise a rigid plastic box fabricated from high temperature plastic on the bottom and lower sides and a lower temperature shrinkable plastic in the remaining areas so as to facilitate the steam penetration and plastic encapsulation of the sterilized infectious waste as well as the compaction thereof by the waste container. Alternatively, waste container 30 could be fabricated from other materials such as cardboard to contain the melting plastic component of the infectious waste during treatment thereof in microwave autoclave apparatus 10.

In use, the apparatus of the present invention is used to sterilize infectious waste of the type including at least 20% by weight of plastic materials therein (and probably 30% or more by weight). The sterilized infectious waste is then densified by the very high pressure and temperature within apparatus 10 into a "brick" or other unitary mass wherein the melted plastic components serve to encapsulate the residual waste and therefore to prevent reinoculation and pontification of the sterilized waste. Moreover, the densification of infectious waste typically results in a significant volume reduction (which can be up to about 75%) in the formation of a unitary mass or "brick" of sterilized waste. The reduced volume and easy to handle unitary mass or "brick" may then be either directly transported to a landfill site for disposal, or fed to a shredder and the shredded elements taken to a landfill or separated into their constituent components for recycling.

Figure 2:
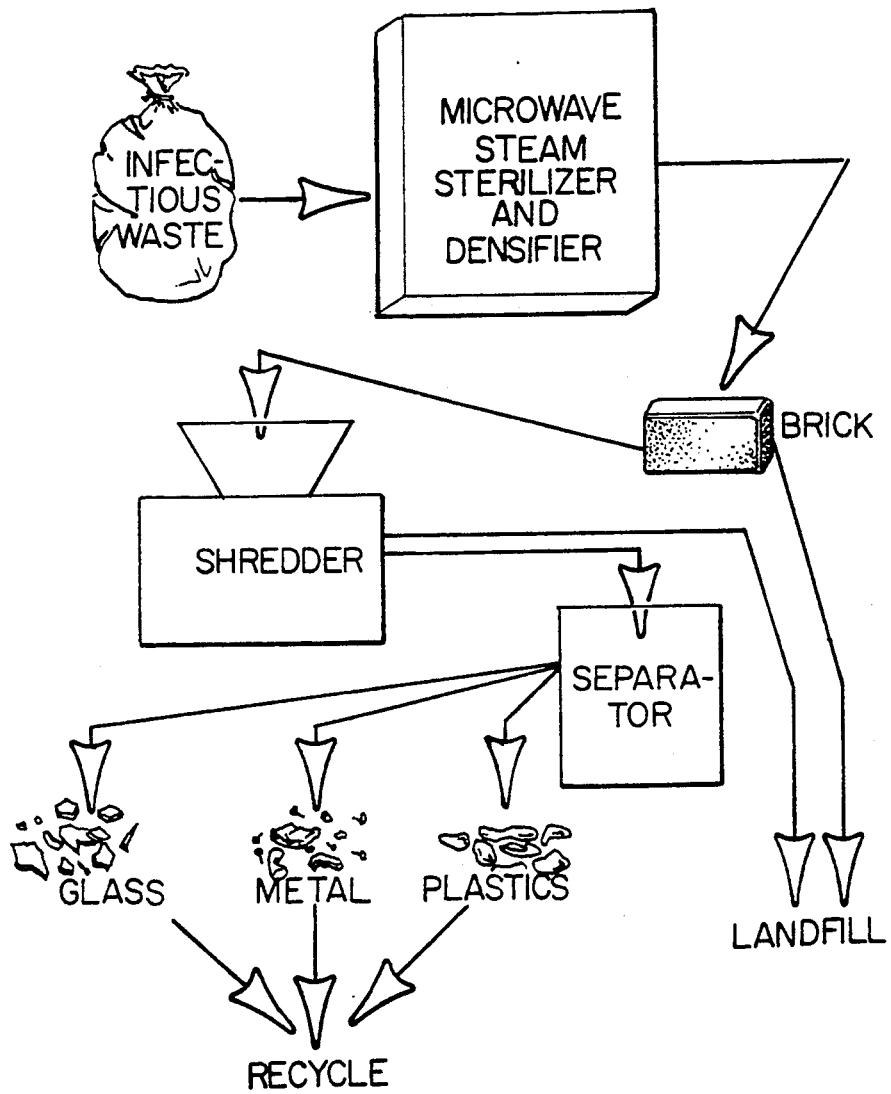
FIG. 2 is a schematic view of a process for handling of infectious waste in accordance with the present invention.

Referring now to both FIGS. 1 and 2, applicant's method to decontaminate and dispose of infectious waste utilizing steam created by microwave energy can be fully appreciated. First of all, the container of infectious waste 30 is suitably placed in microwave autoclave apparatus 10 and the apparatus sealed. Once the waste container 30 of infectious waste has been placed in microwave autoclave apparatus 10, the air may be removed from pressure vessel 12 by means of vacuum pump 20. In the alternative, the air may be left in pressure vessel 12. The advantage of removing the air, as noted above, is that a vacuum allows for lower air pressure to achieve a desired temperature as well as obviating air pockets in the infectious waste which can impede effective sterilization thereof.

After the air has been removed from pressure vessel 12 by vacuum pump 20, a selected amount of water is introduced by water inlet 18. Water inlet 18 may be positioned so that it will introduce water adjacent pressure vessel insert 16 or, in the alternative, water inlet 18 may be positioned so as to introduce water directly into pressure vessel insert 16 in which infectious waste has been positioned. Thus, as a matter of choice, the water may be introduced so as to surround pressure vessel insert 16, or to be in contact with the infectious waste, or both. Once the water has been introduced, microwave energy source 22 is actuated so as to heat the water and create both high temperature and high pressure within pressure vessel 12 which serves to sterilize the infectious waste. The preferred temperature is at least 150° C. and the preferred pressure is at least 54 psig, and the maximum desired temperature is about 200° C. and the maximum desired pressure is about 210 psig.

Figure 4:
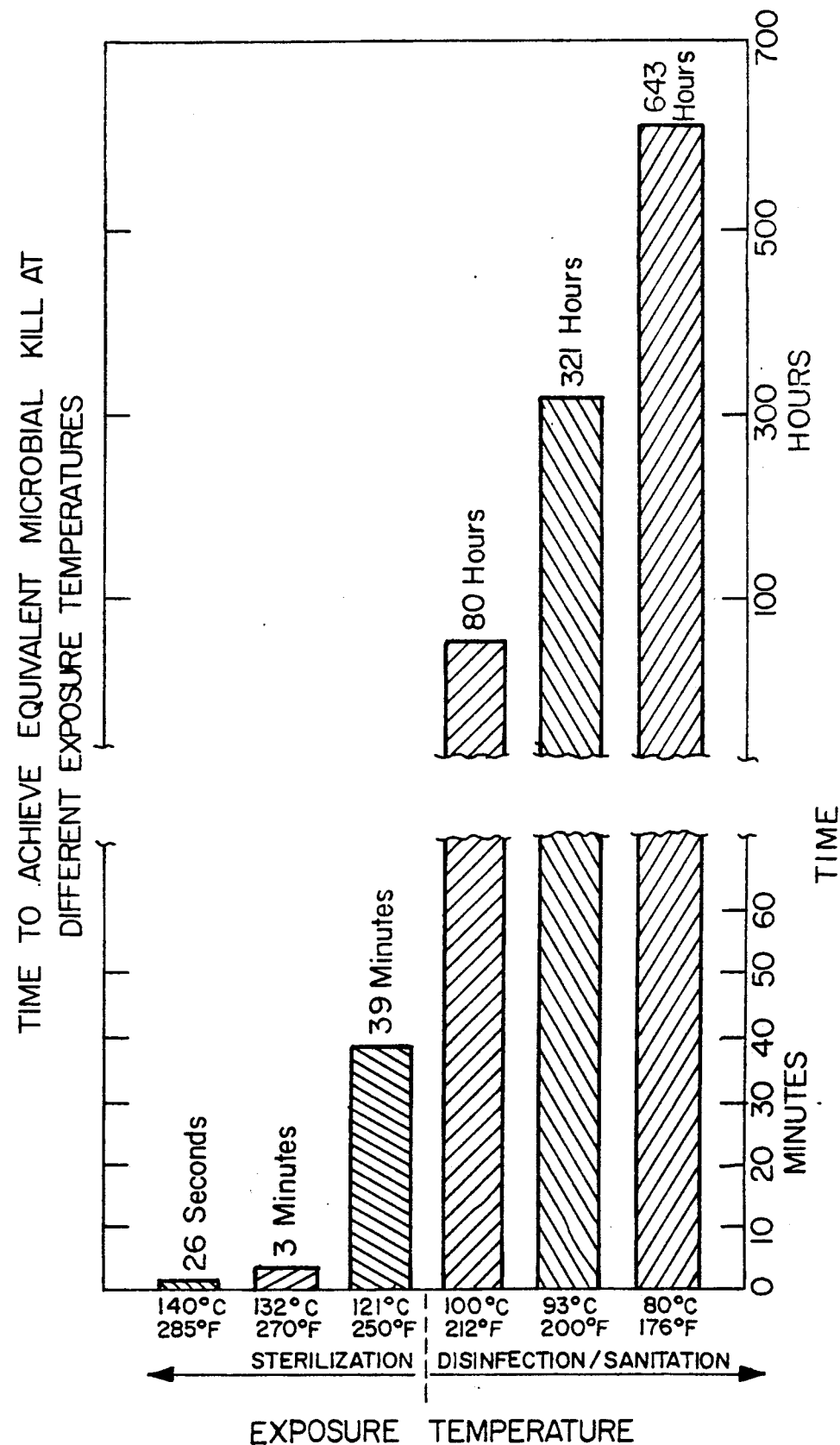
FIG. 4 is a chart illustrating the effect of temperature on time required for microbial kill.

The microwave energy is particularly effective at sterilizing the infectious waste since, unlike conventional steam sterilization, the microwave energy will serve to explode sealed ampoules and the like as well as very effectively seek out and vaporize all liquids in the infectious waste. Thus, the sterilization effected by the microwave energy is more effective at accomplishing sterility than a conventional autoclave which is operated in the range of 121°-150° C. and 15-54 psig. With reference to FIG. 4 of the drawings, it can be appreciated why the higher temperatures of the present invention are so effective and time efficient in sterilizing the infectious waste.

During sterilization, time, temperature, pressure, humidity, and reflected microwave energy are monitored by monitor 24 which is electrically connected with microwave energy source 22 and microprocessor 26 so that microprocessor 26 will deactuate microwave energy source 22 when a predetermined temperature (for example 200° C.) is obtained.

Due to the high operating temperature and pressure of the microwave autoclave apparatus of the invention, the plastics (at least 20% and typically 30% or more by weight) of the infectious waste will melt and serve to encapsulate the remaining sterilized infectious waste during the densification portion of the treatment process subsequent to sterilization. Depending on the type of container 30 in which the infectious waste is positioned, the resulting treated infectious waste product may assume a "brick" or other unitary mass form for further processing. A plastic-coated unitary mass, preferably in "brick" form, ensures that the residual sterilized waste does not become reinoculated.

Optionally, water may be introduced through water inlet 18 to cool the waste. The water is vaporized into steam by the hot waste, and the steam is suitably released through petcocks (not shown) into the atmosphere to facilitate prompt cooling of the treated waste.

The unitary mass or "brick" of treated infectious waste (which results from a volume reduction of up to 75% a landfill or it may be first shredded and then sent to the landfill. In the alternative, the unitary mass or "brick" of treated infectious waste may be shredded and the shredded material sorted out into its constituent elements and then recycled.

The advantages of the apparatus and method of the present invention include the following:
1. Penetration of fluidly sealed waste elements which cannot normally be penetrated by externally generated steam.
2. The fact that the infectious waste is dried by the microwave and no hot water remains in the treated infectious waste material.
3. The microwave energy produced by the apparatus is focused on the infectious waste and water to efficiently generate steam for microbial sterilization.
4. The high strength plastic pressure vessel can be operated at higher temperatures and pressures than conventional steam autoclaves so as to allow unique sterilizing conditions wherein the steam is used to melt the plastic components of the waste to form a "brick" or other unitary mass in order to reduce the waste volume up to about 75% subsequent to sterilization.
5. The high strength plastics used in the pressure vessel of the invention allow for high operating temperatures and pressure and significantly reduce treatment time to sterilize infectious waste.
6. Condensed water from steam cooled by lower temperature wastes will be rapidly reheated by the microwave energy for enhanced efficiency.
7. The microwave energy will explode and/or melt liquid-containing glass, plastic, or microtransparent vials in the infectious waste.

8. The encapsulation of the treated waste in the melted plastic prevents reinoculation of the waste.
9. The unitary mass or "bricks" of waste as well as the shredded remnants thereof reduce landfill space requirements.

It will be understood that various details of the invention may be changed without departing from the scope of the invention. Furthermore, the foregoing description is for the purpose of illustration only, and not for the purpose of limitation—the invention being defined by the claims.

What is claimed is:

1. A process for microwave sterilization and densification of infectious waste, said process comprising the steps of:
   providing a supply of infectious waste to be sterilized and disposed of, said infectious waste including at least 20% by weight of plastic materials therein;
   placing a selected portion of said infectious waste into a pressure vessel of a microwave sterilizer and then sealing said sterilizer;
   introducing a selected amount of water into the sealed pressure vessel to facilitate treatment of the infectious waste contained therein;
   actuating the microwave sterilizer so as to transform the water in said pressure vessel into steam and thereby to elevate the temperature within said pressure vessel to at least 150° C. and the pressure to at least 54 psig;
   sterilizing the infectious waste within said pressure vessel;
   densifying the infectious waste within said pressure vessel by melting the plastic materials contained therein and forming a unitary mass of reduced volume wherein said melted plastic substantially encases the residual sterilized infectious waste components; and
   removing the unitary mass of hazardous waste from said microwave sterilizer.

2. A process for microwave sterilization and disposal of infectious waste according to claim 1 wherein said infectious waste is selected from the group consisting of isolation wastes; cultures and stocks of infectious agents and associated biologicals; human blood and blood products; pathological waste; contaminated sharps; contaminated animal carcasses, body parts, and bedding; wastes from surgery and autopsy; miscellaneous laboratory wastes; dialysis unit wastes; contaminated equipment; and mixtures thereof.

3. A process for microwave sterilization and disposal of infectious waste according to claim 2 wherein said infectious waste includes at least 30% by weight of plastic materials therein.

4. A process for microwave sterilization and disposal of infectious waste according to claim 1 wherein said selected portion of infectious waste is first placed into a container prior to placement into the pressure vessel of the microwave sterilizer.

5. A process for microwave sterilization and disposal of infectious waste according to claim 4 wherein said container comprises plastic wherein at least a portion thereof will melt during sterilization and densification of said infectious waste.

6. A process for microwave sterilization and disposal of infectious waste according to claim 4 wherein said container comprises cardboard or the like.

7. A process for microwave sterilization and disposal of infectious waste according to claim 1 including the step of removing the air from said pressure vessel with a vacuum pump prior to treatment of said infectious waste therein.

8. A process for microwave sterilization and disposal of infectious waste according to claim 1 including the step of monitoring the temperature and pressure within said pressure vessel during said infectious waste sterilization and disposal process.

9. A process for microwave sterilization and disposal of infectious waste according to claim 8 including providing computer control means to deactuate said microwave sterilizer when certain predetermined limits of temperature and/or pressure are monitored.

10. A process for microwave sterilization and disposal of infectious waste according to claim 1 wherein said densification reduces the volume of said infectious waste mass by up to 75%.

11. A process for microwave sterilization and disposal of infectious waste according to claim 1 wherein said unitary mass of sterilized and densified infectious waste substantially defines a brick-like shape.

12. A process for microwave sterilization and disposal of infectious waste according to claim 1 wherein said unitary mass is removed to a landfill or the like for disposal thereof.

13. A process for microwave sterilization and disposal of infectious waste according to claim 1 including the step of shredding said unitary mass subsequent to removal from said microwave sterilizer.

14. A process for microwave sterilization and disposal of infectious waste according to claim 13 wherein said shredded unitary mass is removed to a landfill or the like for disposal thereof.

15. A process for microwave sterilization and disposal of infectious waste according to claim 13 wherein said shredded unitary mass is separated into its basic constituent elements which are then suitably recycled.

16. A process for microwave sterilization and densification of infectious waste, said process comprising the steps of:
   providing a supply of infectious waste to be sterilized and disposed of, said infectious waste including at least 20% by weight of plastic materials therein;
   placing a selected portion of said infectious waste into a container which is then placed into the pressure vessel of a microwave sterilizer and then sealing said sterilizer;
   removing the air from said pressure vessel with a vacuum pump in fluid communication therewith;
   introducing a selected amount of water into the sealed pressure vessel to facilitate treatment of the infectious waste contained therein;
   actuating the microwave sterilizer so as to transform the water an said pressure vessel into steam and thereby to elevate the temperature within said pressure vessel to at least 150° C. and the pressure to at least 54 psig;
   sterilizing the infectious waste within said pressure vessel;
   densifying the infectious waste within said pressure vessel by melting the plastic materials contained therein and forming a unitary mass of reduced volume wherein said melted plastic substantially encases the residual sterilized infectious waste components;
   monitoring the temperature and pressure within said pressure vessel during said sterilization and densification;

removing the unitary mass of hazardous waste from said microwave sterilizer.

17. A process for microwave sterilization and disposal of infectious waste according to claim 16 wherein said infectious waste is selected from the group consisting of isolation wastes; cultures and stocks of infectious agents and associated biologicals; human blood and blood products; pathological waste; contaminated sharps; contaminated animal carcasses, body parts, and bedding; wastes from surgery and autopsy; miscellaneous laboratory wastes; dialysis unit wastes; contaminated equipment; and mixtures thereof.

18. A process for microwave sterilization and disposal of infectious waste according to claim 11 wherein said infectious waste container comprises plastic wherein at least a portion thereof will melt during sterilization and densification of said infectious waste.

19. A process for microwave sterilization and disposal of infectious waste according to claim 16 wherein said infectious waste container comprises cardboard or the like.

20. A process for microwave sterilization and disposal of infectious waste according to claim 12 including providing computer control means to deactuate said microwave sterilizer when certain predetermined limits of temperature and/or pressure are monitored.

21. A process for microwave sterilization and disposal of infectious waste according to claim 16 wherein said densification reduces the volume of said infectious waste mass by up to 75%.

22. A process for microwave sterilization and disposal of infectious waste according to claim 16 wherein said unitary mass of sterilized and densified infectious waste substantially defines a brick-like shape.

23. A process for microwave sterilization and disposal of infectious waste according to claim 16 wherein said unitary mass is removed to a landfill or the like for disposal thereof.

24. A process for microwave sterilization and disposal of infectious waste according to claim 16 including the step of shredding said unitary mass subsequent to removal from said microwave sterilizer.

25. A process for sterilization and disposal of infectious waste according to claim 24 wherein said shredded unitary mass is removed to a landfill or the like for disposal thereof.

26. A process for microwave sterilization and disposal of infectious waste according to claim 24 wherein said shredded unitary mass is separated into its basic constituent elements which are then suitably recycled.

* * * * *